(12) United States Patent
Hoshinouchi

(10) Patent No.: US 9,011,351 B2
(45) Date of Patent: Apr. 21, 2015

(54) GUIDEWIRE INSERTION AID

(75) Inventor: Yuya Hoshinouchi, Fukuroi (JP)

(73) Assignee: Covidien LP, Mansfield, MA (US)

( * ) Notice: Subject to any disclaimer, the term of this patent is extended or adjusted under 35 U.S.C. 154(b) by 551 days.

(21) Appl. No.: 13/214,530

(22) Filed: Aug. 22, 2011

(65) Prior Publication Data

US 2012/0078231 A1    Mar. 29, 2012

(30) Foreign Application Priority Data

Sep. 24, 2010    (JP) ................................ 2010-213532

(51) Int. Cl.
| | | |
|---|---|---|
| *A61B 5/00* | (2006.01) | |
| *A61M 25/00* | (2006.01) | |
| *A61M 25/09* | (2006.01) | |

(52) U.S. Cl.
CPC .............................. *A61M 25/09041* (2013.01)

(58) Field of Classification Search
CPC ........... A61B 5/6851; A61B 2017/003; A61B 2017/00469; A61M 25/09; A61M 25/09041; A61M 25/0905; A61M 2025/09; A61M 2025/09108; A61M 2025/09116; A61M 2025/09125
USPC ........................................................ 600/585
See application file for complete search history.

(56) References Cited

U.S. PATENT DOCUMENTS

| | | | |
|---|---|---|---|
| 3,561,445 A | 2/1971 | Katerndahl et al. | |
| 3,995,628 A | 12/1976 | Gula et al. | |
| 4,860,757 A | 8/1989 | Lynch et al. | |
| 4,917,094 A | 4/1990 | Lynch et al. | |
| 5,125,905 A | 6/1992 | Wright et al. | |
| 5,125,906 A | 6/1992 | Fleck | |
| 5,137,288 A | 8/1992 | Starkey et al. | |
| 5,137,517 A | 8/1992 | Loney et al. | |
| 5,161,534 A | 11/1992 | Berthiaume | |

(Continued)

FOREIGN PATENT DOCUMENTS

| | | |
|---|---|---|
| JP | 2002-282275 A | 10/2002 |
| JP | 05-208051 B2 | 6/2013 |

OTHER PUBLICATIONS

Japanese Patent Office Website Japanese to English Machine Translation of JP 2002-282275. Accessed on Feb. 7, 2014.*

(Continued)

*Primary Examiner* — Adam Eiseman
(74) *Attorney, Agent, or Firm* — Alana T. Bergman, Esq.

(57) ABSTRACT

[Issue] To provide a guidewire insertion aid which is very easy to operate because a lubricated guidewire can be easily fed out.
[Means of Resolution] A guidewire insertion aid 11 according to the present invention is used for feeding out a guidewire 1 inserted in a housing 2 in order to insert said guidewire into the lumen of a piece of medical equipment. The insertion aid 11 comprises: a main body 21, a housing support part 22 and a guidewire support part 26. A sliding contact part 28 is disposed between the housing support part 22 and the guidewire support part 26. The sliding contact part 28 extends in the lengthwise direction of the main body and has a sliding contact surface 28 for the guidewire 1. A feed-out member 51 is provided on the main body 21 and has a water-retentive water-retention member 52. The feed-out member 51 is disposed with the water-retention member 52 side thereof facing towards the sliding contact surface 29. The feed-out member 51 can be displaced while the guidewire 1 is held between said feed-out member and the sliding contact part 28.

15 Claims, 6 Drawing Sheets

(56) References Cited

U.S. PATENT DOCUMENTS

| | | |
|---|---|---|
| 5,186,179 A | 2/1993 | MacEachern |
| 5,242,428 A * | 9/1993 | Palestrant .................... 604/265 |
| 5,263,938 A | 11/1993 | Orr et al. |
| 5,273,042 A | 12/1993 | Lynch et al. |
| 5,279,573 A | 1/1994 | Klosterman |
| 5,282,479 A | 2/1994 | Havran |
| 5,318,541 A | 6/1994 | Viera et al. |
| 5,325,746 A | 7/1994 | Anderson |
| 5,325,868 A | 7/1994 | Kimmelstiel |
| 5,366,441 A | 11/1994 | Crawford |
| 5,366,444 A | 11/1994 | Martin |
| 5,438,993 A | 8/1995 | Lynch et al. |
| 5,443,081 A | 8/1995 | Klosterman |
| 5,448,993 A | 9/1995 | Lynch et al. |
| 5,454,785 A | 10/1995 | Smith |
| 5,462,527 A | 10/1995 | Stevens-Wright et al. |
| 5,484,419 A | 1/1996 | Fleck |
| 5,507,300 A | 4/1996 | Mukai et al. |
| 5,507,728 A | 4/1996 | Erskine |
| 5,634,475 A | 6/1997 | Wolvek |
| 5,730,150 A | 3/1998 | Peppel et al. |
| 5,810,012 A | 9/1998 | Lynch et al. |
| 5,810,835 A | 9/1998 | Ryan et al. |
| 5,827,202 A | 10/1998 | Miraki et al. |
| 5,843,002 A | 12/1998 | Pecor et al. |
| 6,011,988 A | 1/2000 | Lynch et al. |
| 6,030,349 A | 2/2000 | Wilson et al. |
| 6,093,179 A | 7/2000 | O'Hara et al. |
| 6,139,540 A | 10/2000 | Rost et al. |
| 6,190,333 B1 | 2/2001 | Valencia |
| 6,228,049 B1 | 5/2001 | Schroeder et al. |
| 6,477,402 B1 | 11/2002 | Lynch et al. |
| 6,533,772 B1 | 3/2003 | Sherts et al. |
| 6,551,281 B1 | 4/2003 | Raulerson et al. |
| 6,558,060 B1 * | 5/2003 | Raju .............................. 401/10 |
| 6,582,390 B1 | 6/2003 | Sanderson |
| 6,641,563 B1 | 11/2003 | Vitullo et al. |
| 7,144,378 B2 | 12/2006 | Arnott |
| 7,191,900 B2 | 3/2007 | Opie et al. |
| 7,331,966 B2 | 2/2008 | Soma et al. |
| 7,357,787 B2 | 4/2008 | Moss |
| 7,455,660 B2 | 11/2008 | Schweikert et al. |
| 2003/0036712 A1 | 2/2003 | Heh et al. |
| 2003/0078563 A1 | 4/2003 | Hamilton |
| 2004/0006329 A1 | 1/2004 | Scheu |
| 2004/0073108 A1 | 4/2004 | Saeed et al. |
| 2004/0082880 A1 | 4/2004 | Heh et al. |
| 2004/0122416 A1 | 6/2004 | Schweikert et al. |
| 2004/0230136 A1 | 11/2004 | Corrigan, Jr. |
| 2005/0020940 A1 | 1/2005 | Opie et al. |
| 2005/0049572 A1 | 3/2005 | Schweikert et al. |
| 2005/0070820 A1 | 3/2005 | Boutillette et al. |
| 2005/0096566 A1 | 5/2005 | Arnott |
| 2005/0171568 A1 | 8/2005 | Duffy |
| 2005/0178684 A1 | 8/2005 | Kesler et al. |
| 2005/0245847 A1 | 11/2005 | Schaeffer |
| 2005/0256374 A1 | 11/2005 | Long et al. |
| 2005/0256429 A1 | 11/2005 | Long et al. |
| 2005/0256504 A1 | 11/2005 | Long et al. |
| 2005/0256505 A1 | 11/2005 | Long et al. |
| 2005/0256506 A1 | 11/2005 | Long et al. |
| 2005/0256507 A1 | 11/2005 | Long et al. |
| 2005/0277851 A1 | 12/2005 | Whittaker et al. |
| 2006/0025705 A1 | 2/2006 | Whittaker et al. |
| 2006/0025721 A1 | 2/2006 | Duffy et al. |
| 2006/0149292 A1 | 7/2006 | Knudtson et al. |
| 2006/0253048 A1 | 11/2006 | Jones et al. |
| 2006/0271085 A1 | 11/2006 | Siess et al. |
| 2007/0032759 A1 | 2/2007 | Falwell et al. |
| 2007/0043307 A1 | 2/2007 | Raulerson et al. |
| 2007/0060878 A1 | 3/2007 | Bonnette et al. |
| 2007/0179472 A1 | 8/2007 | Whittaker et al. |
| 2007/0185413 A1 | 8/2007 | Asai et al. |
| 2007/0219467 A1 | 9/2007 | Clark et al. |
| 2007/0225615 A1 | 9/2007 | Chechelski et al. |
| 2008/0097331 A1 | 4/2008 | Spivey et al. |
| 2008/0097465 A1 | 4/2008 | Rollins et al. |
| 2008/0154190 A1 | 6/2008 | St. Germain et al. |
| 2008/0228145 A1 | 9/2008 | Watson |
| 2008/0275481 A1 | 11/2008 | Scarpone |
| 2008/0300574 A1 | 12/2008 | Belson et al. |

OTHER PUBLICATIONS

European Search Report corresponding to European Application No. EP 11 18 0406.8, completed Dec. 12, 2011 and mailed Dec. 28, 2011; 7 pages.

Notification of the Third Office Action, and translation thereof, from counterpart Chinese Patent Application No. 201110284651.4, dated Jan. 29, 2015, 17 pp.

* cited by examiner

GUIDEWIRE INSERTION AID

TECHNICAL FIELD

The present invention relates to a guidewire insertion aid for inserting a guidewire into the lumen of a piece of medical equipment.

PRIOR ART

When medical procedures are undertaken, it is sometimes conventionally necessary to insert a guidewire into the lumen of a piece of medical equipment. A guidewire is normally housed inserted in a tubular housing. A guidewire insertion aid for assisting in the operation to feed out the guidewire is then attached to the housing (see Patent Document 1, for example). A conventional guidewire insertion aid comprises a main body and a housing support part is provided at the base end of the main body. The housing for housing the metal guidewire is detachably supported by the housing support part. A cylindrical guidewire support part which is open at the tip end is provided at the tip end of the main body. The guidewire which has been fed out from the housing is inserted into and supported by the guidewire support part. A sliding contact part having a sliding contact surface is provided in the main body between the housing support part and the guidewire support part.

The following procedure is carried out when the guidewire is inserted into the body using this kind of guidewire insertion aid, for example. A practitioner first of all grips the main body, pinching it with the fingers of one hand in such a way that the guidewire support part is at the front. The practitioner then moves his or her thumb forwards in order to feed the guidewire outwards and forwards so that it projects from the tip end of the guidewire support part.

Furthermore, in addition to the abovementioned type of metal guidewire, there are also those that are known as lubricated guidewires having a structure in which a coating of lubricant is applied to the surface of the wire. There are also devices which are known in the art for providing lubrication by wetting the lubricated guidewire (see Patent Document 2, for example). These types of devices enable smooth insertion of the lubricated guidewire.

PRIOR ART DOCUMENTS

Patent Documents

[Patent Document 1] Japanese Unexamined Utility Model Application Publication H7-22752
[Patent Document 2] U.S. Pat. No. 5,242,428

DISCLOSURE OF THE INVENTION

Issues to be Resolved by the Invention

However, when conventional guidewire insertion aids are used, the practitioner's fingers end up slipping over the lubricated guidewire and the sliding contact surface when he or she attempts to push out the lubricated guidewire. This means that it is not possible to feed out the lubricated guidewire in the skilful manner which would be possible with a metal guidewire. It is therefore not possible to use a conventional unmodified metal guidewire insertion aid, and it is necessary to use an insertion aid especially for lubricated guidewires. Accordingly, in such cases, the practitioner needs to carry out an operation by holding the device with one hand while feeding out the lubricated guidewire with the other hand, which unfortunately occupies both hands. As a result there are problems in terms of ease of operation.

The present invention has been devised in view of the issues outlined above, and the object thereof lies in providing a guidewire insertion aid which is very easy to operate because the lubricated guidewire can be easily fed out.

Means of Resolving the Issues

The following means 1 to 6 are given as means for resolving the issues outlined above.

[1] A guidewire insertion aid for feeding out a guidewire inserted in a housing in order to insert said guidewire into the lumen of a piece of medical equipment, said guidewire insertion aid being characterized in that it comprises: a main body having a tip end part and a base end part; a housing support part which is provided at the base end part in order to detachably support the housing on the main body; a guidewire support part of cylindrical shape and open at the tip end, which is provided at the tip end part in order to support the guidewire passing therethrough which has been fed out from the housing; a sliding contact part which is disposed between the housing support part and the guidewire support part, and extends in the lengthwise direction of the main body and has a guidewire sliding contact surface; and a feed-out member which is provided on the main body and has a water-retentive water-retention member, wherein the feed-out member is disposed with the water-retention member side thereof facing towards the sliding contact surface, and can be displaced while the guidewire is held between said feed-out member and the sliding contact part.

Therefore, according to the invention disclosed in means 1, the water-retention member side of the feed-out member and the sliding contact surface side of the sliding contact part are disposed facing towards each other, and the feed-out member is displaced with a finger in the lengthwise direction while the guidewire is held between the above members. When this operation is carried out, the guidewire can be fed out at the tip end side of the main body by way of the feed-out member. The water-retention member of the feed-out member is water-retentive and therefore able to hold liquid for lubrication. This means that when the feed-out operation is carried out using the feed-out member, the guidewire can be fed out while retaining lubricating properties as a result of contact between the water-retention member and the guidewire. Furthermore, this configuration makes it possible for the practitioner to feed out the guidewire using a finger, without directly contacting the guidewire. As described above, the insertion aid of means 1 makes it possible for a lubricated guidewire to be easily fed out, and is therefore very easy to operate.

[2] A guidewire insertion aid according to means 1, characterized in that feed-out member support parts having a guide part which extends in the lengthwise direction of the main body are provided on the main body above where the sliding contact part is located; and the feed-out member is a feed-out block having the water-retention member on the lower surface thereof, and is supported by the feed-out member support parts in such a way as to be able to move forwards or backwards in the lengthwise direction of the main body.

Therefore, according to the invention disclosed in means 2, the water-retention member side of the feed-out block and the sliding contact surface side of the sliding contact part are disposed beforehand facing towards each other. The feed-out block is then moved forwards or backwards using a finger while the guidewire is held between the above members. When this operation is carried out, the guidewire can be fed out at the tip end side of the main body by way of the feed-out block. The feed-out block is guided by means of the guide part while being supported by the feed-out member support parts, and therefore it is possible to achieve reliable back-and-forth movement in the lengthwise direction of the main body.

[3] A guidewire insertion aid according to means 2, characterized in that an urging member for urging the feed-out block in the direction of the base end part of the main body is provided between the feed-out block and the feed-out member support part.

Therefore, according to the invention disclosed in means 3, the feed-out block is moved outwardly using a finger in order to feed out the guidewire at the tip end side of the main body, after which, when the finger is moved away, the feed-out block is automatically moved in the opposite direction by means of the urging force of the urging member so as to return to its original position. Consequently it is unnecessary to return the feed-out block, and the ease of operation is further improved.

[4] A guidewire insertion aid according to means 1, characterized in that the feed-out member is a feed-out block having the water-retention member on the lower surface thereof, and is linked to the main body by way of a flexible linking member.

Therefore, according to the invention disclosed in means 4, the water-retention member side of the feed-out block and the sliding contact surface side of the sliding contact part are disposed facing towards each other, and the feed-out block is moved forwards or backwards using a finger while the guidewire is held between the above members. When this operation is carried out, the guidewire can be fed out at the tip end side of the main body by way of the feed-out block. Even though the flexible linking member links the main body and the feed-out block, this linking member can deform when the feed-out block moves forwards or backwards. Consequently, there is no obstruction to the back-and-forth movement. Furthermore, this structure involves fewer components and is simpler than the case in which the feed-out member is provided separately.

[5] A guidewire insertion aid according to means 1, characterized in that feed-out member support parts are provided on the main body above where the sliding contact part is located; and the feed-out member is an endless feed-out belt having a water-retention member on the outer peripheral surface thereof, and is supported by the feed-out member support parts in such a way as to be able to move circumferentially.

Therefore, according to the invention disclosed in means 5, the water-retention member side of the feed-out belt and the sliding contact surface side of the sliding contact part are disposed beforehand facing towards each other. The feed-out belt is then moved circumferentially using a finger while the guidewire is held between the above members. When this operation is carried out, the guidewire can be fed out at the tip end side of the main body by way of the feed-out belt.

[6] A guidewire insertion aid according to any one of means 1 to 5, characterized in that a water-retention member is also provided on the sliding contact surface.

Therefore, according to the invention disclosed in means 6, water-retention members come into contact with the guidewire from two directions. Consequently, the guidewire can be reliably lubricated even if the sliding contact surface is short.

Advantages of the Invention

Therefore, according to the inventions disclosed in claims 1 to 6, there is provided a guidewire insertion aid which is very easy to operate because the lubricated guidewire can be easily fed out.

PREFERRED MODES OF EMBODIMENT OF THE INVENTION

First Mode of Embodiment

A guidewire insertion aid 11 according to the first mode of embodiment of the present invention will be described in detail below with reference to FIGS. 1 to 4.

Figure 1:
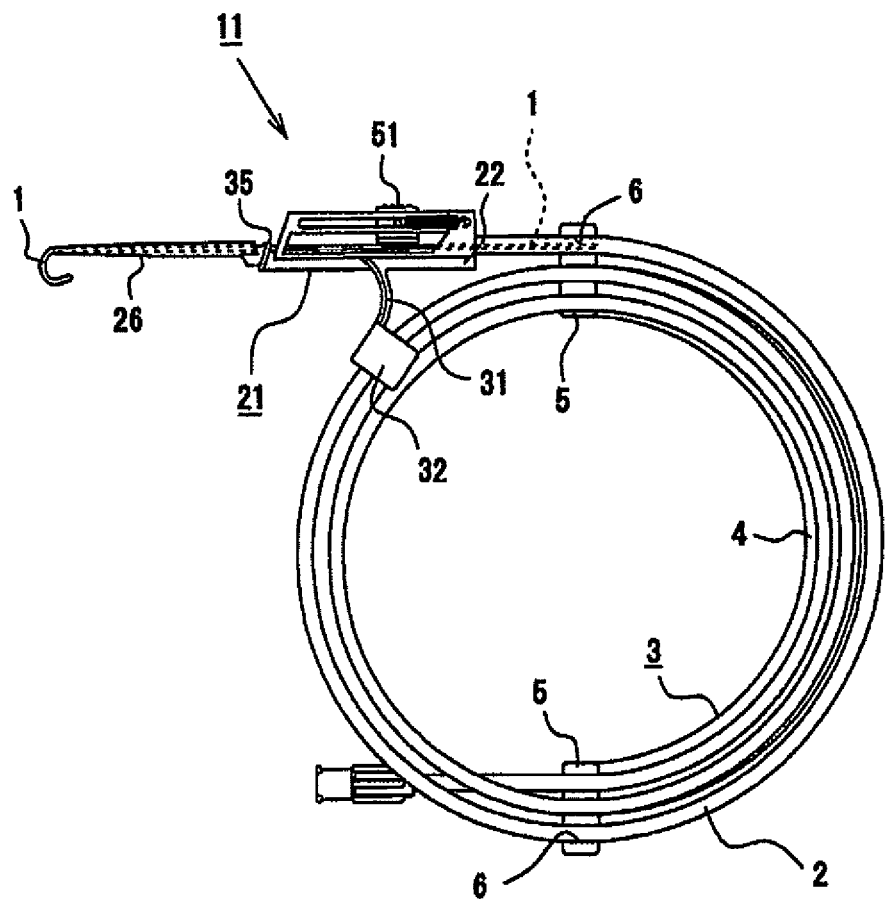
[FIG. 1] is a front view showing the situation when the guidewire insertion aid according to a first mode of embodiment of the present invention is fitted to the housing.

FIG. 1 shows the guidewire insertion aid 11 and housing 2 according to this mode of embodiment. The housing 2 comprises a synthetic resin tube wound into two or three layers in which a guidewire 1 is housed in an inserted state. A synthetic resin holder 3 has the role of retaining the wound form of the housing 2. To be more specific, the holder 3 according to this mode of embodiment comprises a substantially C-shaped base part 4 and a pair of latching parts 5 which are provided at the two ends of the base part 4. A plurality of latching grooves 6 are formed in each of the latching parts 5, and the housing 2 is fitted into and latched by the latching grooves 6. A lubricated guidewire having a structure in which a coating of lubricant is applied to the surface of the wire is used here as the guidewire 1 in this mode of embodiment. Depth marks are marked on the surface of the wire at prescribed lengths. In this mode of embodiment, the tip end of the wire is bent into a J-shape. It should be noted that the tip end of the wire may equally be angled or straight, rather than being J-shaped.

Figure 2:
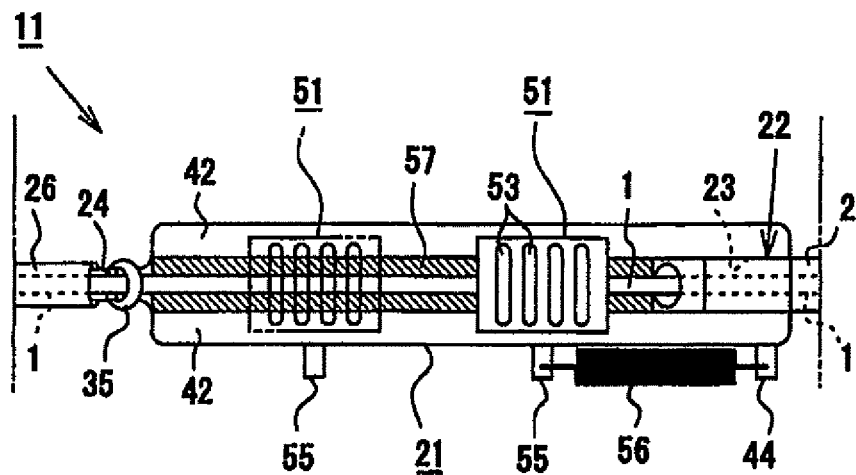
[FIG. 2] is an enlarged plan view of the main parts showing the guidewire insertion aid according to the first mode of embodiment.
Figure 3:
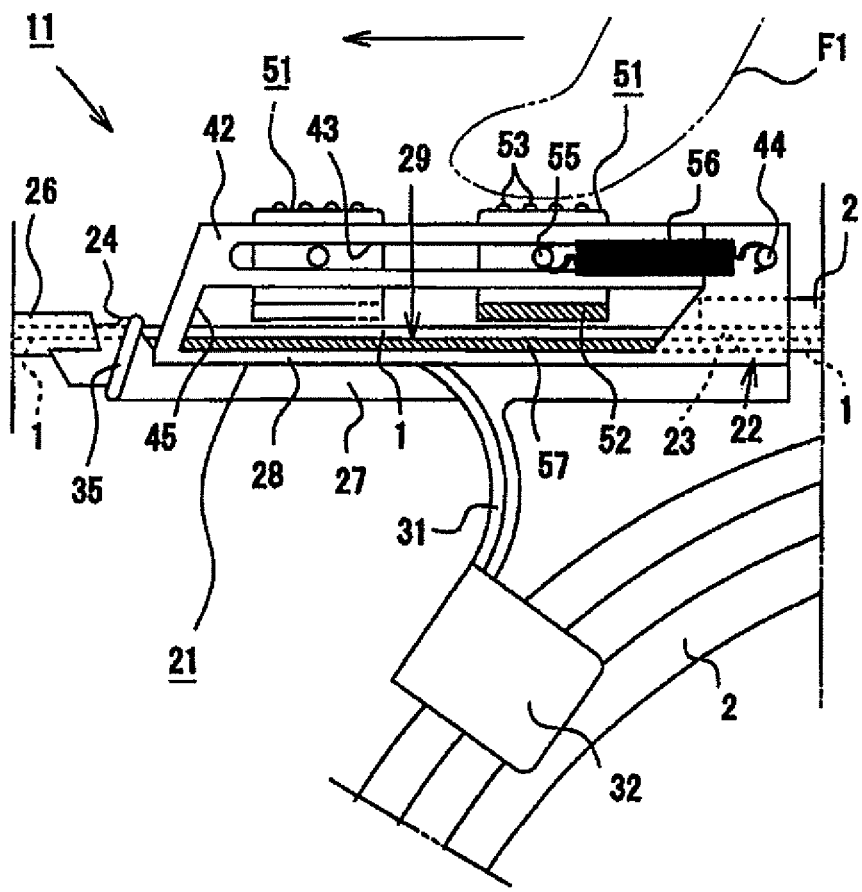
[FIG. 3] is an enlarged front view of the main parts showing the guidewire insertion aid according to the first mode of embodiment.

As shown in FIGS. 1 to 3, the guidewire insertion aid 11 according to this mode of embodiment comprises a main body 21 made of synthetic resin (polypropylene, for example). The main body 21 has a globally elongate shape in the front to rear direction. A housing support part 22 is provided as a single piece at the base end part of the main body 21. One end of the housing 2 is detachably engaged with an engaging hole 23 which forms an opening in the rear end surface of the housing support part 22. The housing 2 is supported in the housing support part 22 by means of this engagement.

A guidewire support part 26 is then provided as a single piece at the tip end part of the main body 21. The diameter of the guidewire support part 26 decreases towards the tip end, and said guidewire support part 26 has a hollow cylindrical shape which is open at the tip end. The guidewire 1 which has been fed out from the housing 2 side passes through the inside of the guidewire support part 26. As a result, the guidewire 1 is supported by the guidewire support part 26.

The main body 21 has, in the centre of the lower surface thereof, a rib 27 which extends in the lengthwise direction of the main body. The presence of the rib 27 increases the overall rigidity of the main body 21. An arm part 31 extending downwards in an arcuate shape is provided as a single piece with the main body 21 and projecting from the lower surface thereof. A holding part 32 having a substantially "⊐"-shaped cross section is provided as a single piece at the tip end of the arm part 31. The holding part 32 holds the housing 2 by means of engagement with the outer peripheral surface of the housing 2. As a result, it is unlikely that positional offset will be produced between the guidewire insertion aid 11 and the housing 2. Furthermore, when the practitioner grasps the guidewire insertion aid 11 with one hand, he or she can hook the fingers other than the thumb F1 on the arm part 31. This means that it is simple for the practitioner to grasp the guidewire insertion aid 11.

As shown in FIGS. 1 to 3, a sliding contact part 28 which extends in the lengthwise direction of the main body is disposed in the main body between the housing support part 22 and the guidewire support part 26. The upper surface of the sliding contact part 28 forms a sliding contact surface 29 with which the guidewire 1 makes sliding contact along the axial direction thereof.

As shown in FIG. 3 etc., a projection 24 which projects slightly towards the upper side of the main body 21 is provided on the main body 21 close to where the guidewire support part 26 is positioned, to be more specific, close to the base end opening of the guidewire support part 26. A rubber ring 35 is then attached correspondingly to the position of the projection 24. If the rubber ring 35 is disposed further to the rear than the projection 24 (the right-hand side in FIGS. 2 and 3), the rubber ring 35 comes into contact with the guidewire 1, which is thereby fixed. A force to return the guidewire 1 to a linear state from the wound state then acts thereon. However, this force alone prevents the guidewire 1 from being fed out naturally. If, on the other hand, the rubber ring 35 is disposed further to the front than the projection 24 (the left-hand side in FIGS. 2 and 3), the rubber ring 35 does not come into contact with the guidewire 1. As a result, the guidewire 1 is released, and the guidewire 1 moves more freely than when it is in the abovementioned state of fixed contact.

As shown in FIGS. 2 and 3, a pair of feed-out member support parts 42 are provided projecting opposite each other with a gap therebetween on the main body 21 above where the sliding contact part 28 is located. A linear guide part 43 extending in the lengthwise direction of the main body is formed at a position on the upper side of each of the pair of feed-out member support parts 42. One of the feed-out member support parts 42 is formed with a latching protrusion 44 close to the end edge of the guide part 43. A window part 45 is formed at a position on the lower side of each of the pair of feed-out member support parts 42.

A feed-out block 51 serving as a feed-out member is supported between the pair of feed-out member support parts 42 in such a way as to be able to move forwards or backwards in the lengthwise direction of the main body. A water-retentive water-retention member 52 is provided on the lower surface of the feed-out block 51. It should be noted that a similar water-retention member 57 is also provided on the sliding contact surface 59 side of the sliding contact part 58. The two water-retention members 52, 57 are disposed opposite each other with the guidewire 1 held therebetween. A plurality of anti-slip protrusions 53 which are intended to improve the ease of operation are provided on the upper surface of the feed-out block 51. A latching protrusion 55 is provided on one side surface of the feed-out block 51. The latching protrusion 55 is disposed in the guide part 43, and the tip end of the latching protrusion 55 exits through the guide part 43, projecting outwards of the feed-out member support parts 42. A coil spring 56 serving as the urging member is provided between the latching protrusion 55 on the feed-out block 51 side and the latching protrusion 44 on the feed-out member support part 42 side. The coil spring 56 serves to apply a spring force which urges the feed-out block 51 in the direction of the base end part of the main body 21.

The water-retention members 52, 57 are preferably formed using a material which is not only water-retentive (water-absorbent), but also has frictional properties (properties such that it does not readily slide). Specifically, a nylon nonwoven fabric or cotton such as gauze, or similar, is preferred as the material for forming these members. That is to say, a fibre assembly such as a fabric is advantageous in that it presents minute surface-unevenness, and therefore suitable frictional properties can be readily achieved. Furthermore, the above-mentioned fibre assembly is advantageous in that it comprises inter-fibre pores, and therefore it readily retains moisture. It should be noted that fibre assemblies in which the fibres themselves are water-absorbent are especially preferred as the material for forming these members.

The method for inserting a catheter employing the above-mentioned guidewire insertion aid 11 will be described below.

The patient's skin around the insertion point is sterilized beforehand, after which a local anaesthetic is applied to the insertion point. A syringe containing heparinized physiological saline or the like is fitted to a cannula for indwelling use in blood vessels and the blood vessel is punctured. Once return-flow of blood has been confirmed, the metal needle of the cannula for indwelling use in blood vessels is held, and the plastic cannula alone is advanced into the blood vessel where it is made indwelling.

The abovementioned guidewire insertion aid 11 is then used to make the guidewire 1 pass through the indwelling cannula, and the guidewire 1 is inserted into the blood vessel.

In this case, one end of the housing 2 in which the guidewire 1 is currently housed is engaged with the engaging hole 23 in the housing support part 22, and the inside of the housing 2 is pre-filled with heparinized physiological saline injected from the other end thereof. If necessary, the water-retention members 52, 57 may also be pre-soaked with physiological saline or heparinized physiological saline. At this point, the rubber ring 35 is still disposed further to the rear than the projection 24, and the guidewire 1 is fixed in such a way that it cannot be naturally fed out. Moreover, it is confirmed that the tip end of the guidewire 1 is inside the guidewire support part 26.

At this point, the practitioner grips the main body 21 with the fingers of one hand in such a way that the guidewire support part 26 is at the front. The tip end of the guidewire support part 26 is then introduced into the plastic cannula, and the rubber ring 35 is positioned further to the front than the projection 24 by pushing the rubber ring 35 upwards using the thumb F1. The guidewire 1 is then fed out in this state. Specifically, as shown in FIG. 3, the pad of the thumb F1 is placed against the upper surface of the feed-out block 51, and the feed-out block 51 is slid towards the tip end side of the main body (i.e. moved outwardly) while being depressed. When this takes place, the guidewire 1 is held between the water-retention member 52 on the feed-out block 51 side and the water-retention member 57 on the contact surface 59 side. The guidewire 1 is then fed out along with the movement of the feed-out block 51. At this point, the water-retention members 52, 57 are in contact with the guidewire 1. Lubrication of the surface of the guidewire 1 is therefore maintained without drying of the physiological saline or heparinized physiological saline. It should be noted that the feed-out block 1 automatically returns to its original position under the spring force of the coil spring 56 when the thumb F1 is removed from the feed-out block 51 which has been slid to the tip end side of the main body.

As a result of carrying out the abovementioned feed-out operation, the guidewire 1 is inserted into the blood vessel through the cannula. When this operation is carried out, radiography should be used in order to confirm that the guidewire 1 is present at the intended position.

Once insertion of the guidewire 1 has been completed, the cannula is withdrawn and a small surgical incision is made at the insertion point using a scalpel for skin incisions. At this point, the subcutaneous tissue and the blood vessel insertion opening are adequately dilated by pressing a dilator forward along the guidewire 1. The dilator is removed after dilation. Next, a catheter whereof the lumen is filled with heparinized physiological saline is slowly inserted along the guidewire 1. In this process, the catheter is pressed forwards up to the intended indwelling position while the depth marks are confirmed. Once it has been confirmed that the catheter is indwelling in the intended position, the guidewire 1 is withdrawn. The air in the lumen of the catheter is then removed by means of a normal method, and the lumen is flushed with physiological saline or heparinized physiological saline in order to prevent coagulation of the blood. At this point radiography is preferably used to confirm that the catheter is not looped inside the body, and that the tip end of the catheter is in the intended position. After this the catheter is secured using a catheter fixing implement and a threaded suture needle together with dressing, and the series of operations for inserting the catheter is complete.

As described above, the following operational advantages are demonstrated with this mode of embodiment.

(1) With the guidewire insertion aid 11 according to this mode of embodiment, the water-retention members 52, 57 come into contact with the guidewire 1 during the feed-out operation employing the feed-out block 51. As a result, the guidewire 1 can be fed out at the tip end side of the main body. Furthermore, this configuration makes it possible for the practitioner to feed out the guidewire 1 without directly contacting the guidewire with his or her thumb F1. This means that the practitioner's thumb F1 does not end up sliding over the guidewire 1 and the sliding contact surface 29, unlike when a conventional guidewire insertion aid is used. Moreover, there is no concern that contact by the thumb F1 will cause a partial loss of lubrication.

As described above, with this guidewire insertion aid 11, the lubricated guidewire 1 can be easily fed out using one hand. This means that both of the practitioner's hands are not occupied during operations, and it is possible to achieve superior ease of operation.

(2) With the guidewire insertion aid 11 according to this mode of embodiment, the feed-out block 1 automatically returns to its original position under the spring force of the coil spring 56 when the thumb F1 is removed after the feed-out block 1 feed-out operation. This means that there is no need to return the feed-out block 51 using the thumb F1, and the ease of operation is further improved.

(3) The guidewire insertion aid 11 according to this mode of embodiment is provided with the rubber ring 35 and the projection 24. Consequently it is possible to fix the guidewire 1 in such a way that it cannot escape, as required. This means that it is possible to prevent in advance a situation such as the guidewire 1 escaping from the tip end of the guidewire insertion aid 11 due to vibration during transportation, for example. It is therefore possible to produce a very reliable product.

(4) The guidewire insertion aid 11 according to this mode of embodiment employs a structure in which the feed-out block 51 is disposed inserted between the pair of feed-out member support parts 42, the linear guide part 43 is provided on the feed-out member support parts 42, and the latching protrusion 55 is disposed on the guide part 43. The feed-out block 51 is therefore guided by means of the guide part 43 while being supported by the pair of feed-out member support parts 42. Consequently it is possible to achieve reliable and smooth back-and-forth movement in the lengthwise direction of the main body.

Figure 4:
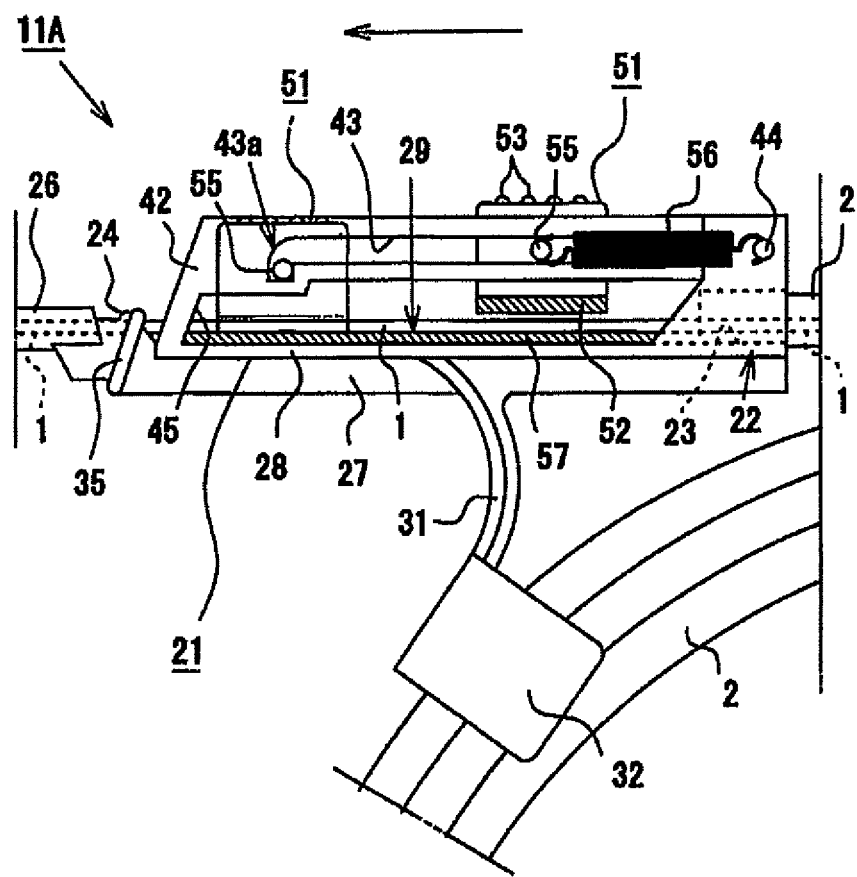
[FIG. 4] is an enlarged front view of the main parts showing the guidewire insertion aid according to a variant example of the first mode of embodiment.

FIG. 4 shows a guidewire insertion aid 11A according to a variant example of the first mode of embodiment. In this variant example the shape of the guide part 43 is slightly different. That is to say, a downwardly curved part 43a is formed at the tip end side of the guide part 43. This means that after the feed-out block 51 has been moved as far as possible to the tip end side of the main body, it can be latched with the latching protrusion 55 received in the curved part 43a. As a result, the feed-out block 51 is held in position at the tip end side of the main body in such a way that it cannot move. Furthermore, the distance between the water-retention member 52 on the feed-out block 51 side and the water-retention member 57 on the sliding contact surface 59 side is reduced. Consequently, the guidewire 1 is reliably pinched between the two so that the guidewire 1 can be made immobile. With this configuration, the feed-out block 51 therefore functions not only as a feed-out member, but also as a guidewire fixing member.

Second Mode of Embodiment

A guidewire insertion aid 71 according to the second mode of embodiment of the invention will be described in detail below with reference to FIGS. 5 and 6.

Figure 5:
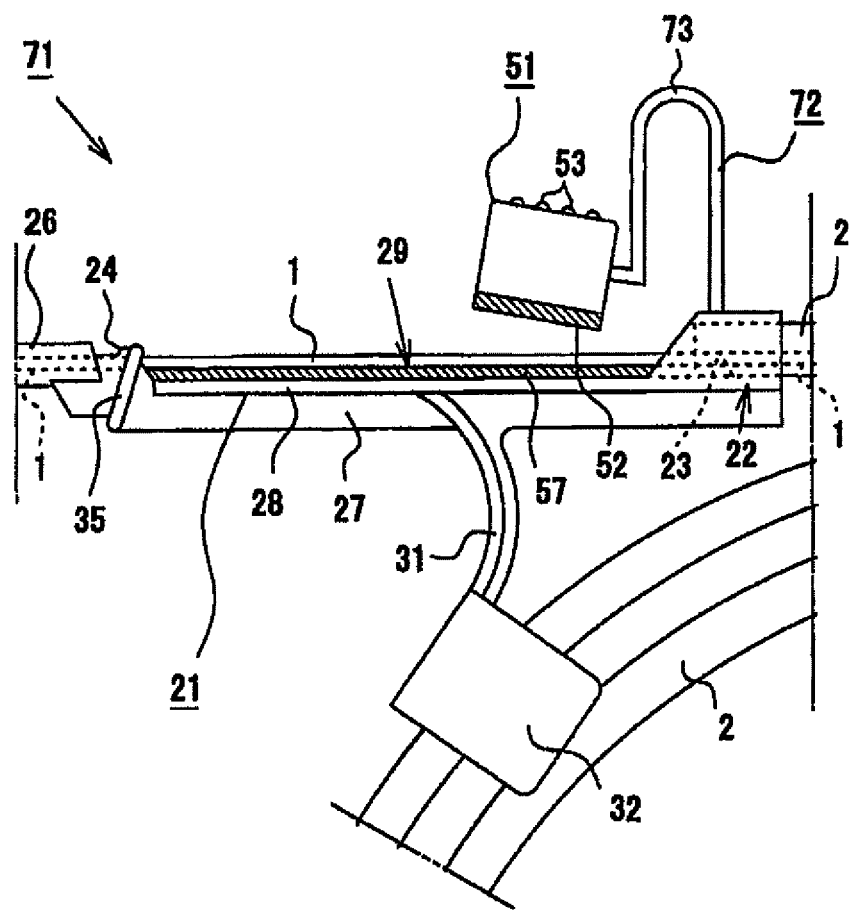
[FIG. 5] is an enlarged front view of the main parts showing the guidewire insertion aid according to the second mode of embodiment.
Figure 6:
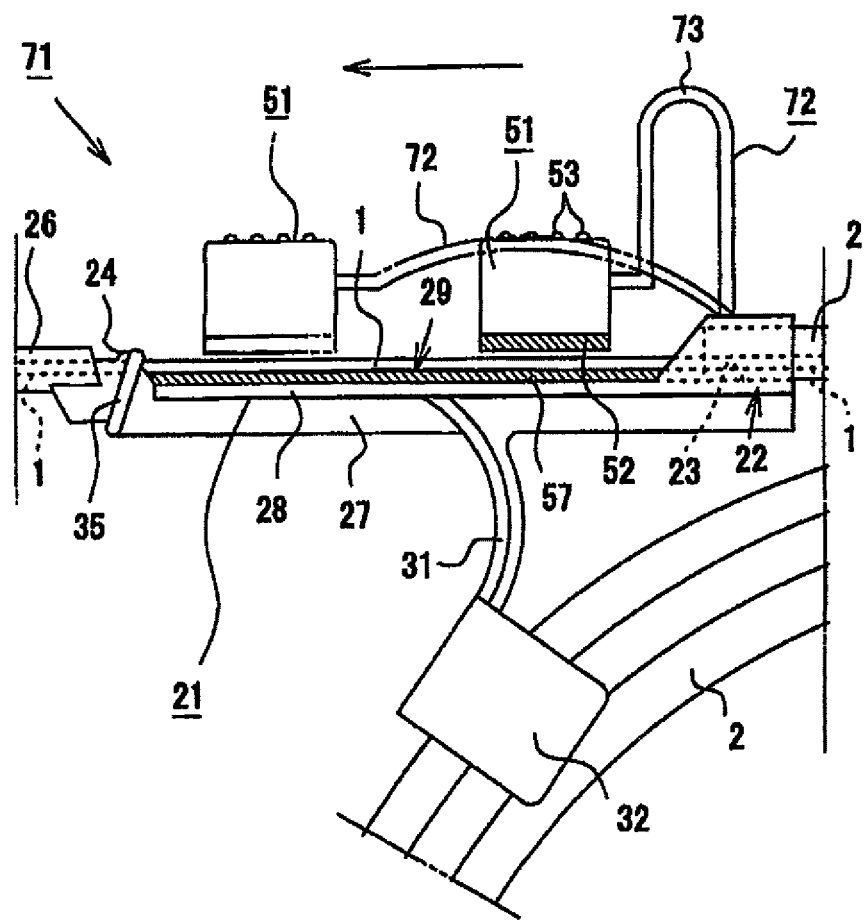
[FIG. 6] is an enlarged front view of the main parts showing the guidewire insertion aid according to the second mode of embodiment.

As shown in FIG. 5, the guidewire insertion aid 71 according to this mode of embodiment comprises a feed-out block 51 having the water-retention member 52 on the lower surface thereof. However, the feed-out member support parts 42 which constitute the structure for supporting the feed-out block 51 are not present. As the support structure used instead of these, the guidewire insertion aid 71 comprises a linking member 72 for linking the feed-out block 51 to the main body 21 side. The linking member 72 according to this mode of embodiment is a flexible strip-like member having a U-shaped curved part 73 midway along. In this instance, the linking member 72 is provided as a single piece with the upper surface of the housing support part 22 of the main body 21. Accordingly, the main body 21 and the linking member 72 are made of a common synthetic resin material (polypropylene) in this mode of embodiment. It should be noted that the linking member 72 may equally be provided as a single piece with the feed-out block 51.

When this guidewire insertion aid 71 is used, the guidewire 1 is held between the water-retention member 52 on the feed-out block 51 side and the water-retention member 57 on the sliding contact part 28 side. In this state, the feed-out block 51 is then moved forwards or backwards using the thumb F1. As a result, the guidewire 1 can be fed out at the tip end side of the main body by way of the feed-out block 51. Even though the flexible linking member 72 links the main body 21 and the feed-out block 51, the curved part 73 is mainly able to extend and contract through deformation when the feed-out block 51 moves forwards or backwards (see FIG. 6). This therefore has the advantage that there is no obstruction to the back-and-forth movement. Furthermore, this structure offers the advantage that there are fewer components and the structure can be simplified, compared with when the feed-out member is a separate component.

Third Mode of Embodiment

A guidewire insertion aid 81 according to the third mode of embodiment of the invention will be described in detail below with reference to FIG. 7.

Figure 7:
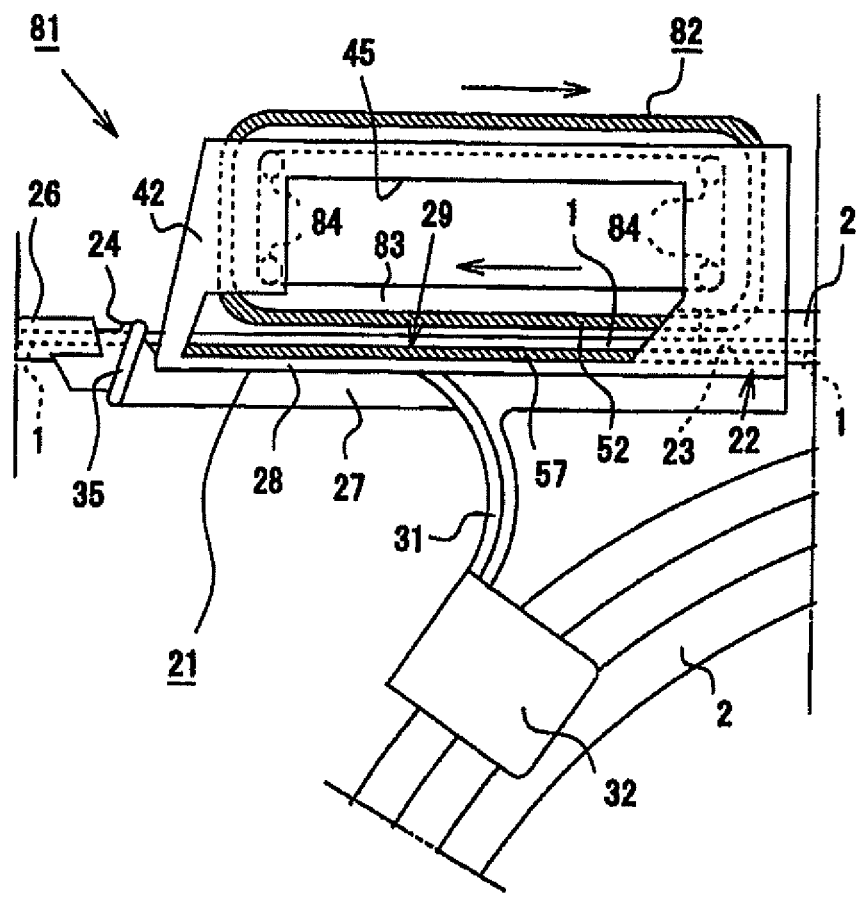
[FIG. 7] is an enlarged front view of the main parts showing the guidewire insertion aid according to the third mode of embodiment.

As shown in FIG. 7, with the guidewire insertion aid 81 according to this mode of embodiment, the pair of feed-out member support parts 42 are provided. However, the structure of the feed-out member supported thereby is very different. That is to say, an endless feed-out belt 82 is used as the feed-out member. This feed-out belt 82 comprises the water-retention member 52 over the whole outer peripheral surface thereof. The water-retention member 52 positioned at the lower surface of the feed-out belt 82 faces the water-retention member on the sliding contact part 28 side. Winding protrusions 84 are provided at four points on the inside surface of the pair of feed-out member support parts 42. The feed-out belt 82 runs around these winding protrusions 84. As a result, the feed-out belt 82 is supported between the pair of feed-out member support parts 42 in a state in which it can move circumferentially.

When this guidewire insertion aid 81 is used, the guidewire 1 is held between the water-retention member of the feed-out belt 82 and the water-retention member 57 on the sliding contact part 28 side. In this state, the feed-out belt 82 is moved circumferentially using the thumb F1. As a result, the guidewire 1 can be fed out at the tip end side of the main body by way of the feed-out belt 82. It should be noted that the part which is operated by the thumb F1 may be on the inner peripheral surface or the outer peripheral surface of the feed-out belt 82. Moreover, the configuration in this mode of embodiment makes it possible to increase the size of the water-retention member 52 on the feed-out belt 82 side. This therefore offers the advantage that the guidewire 1 can be efficiently and reliably lubricated.

Moreover, the modes of embodiment of the present invention may be modified in the following way.

In the first and second modes of embodiment described above, a plurality of anti-slip protrusions 53 were provided on the upper surface of the feed-out block 51, but it is equally possible to employ an anti-slip structure in the form of lugs, holes or grooves etc. Furthermore, this kind of anti-slip structure may also be provided on the inner peripheral surface of the feed-out belt 82 in the third mode of embodiment, for example.

In the first mode of embodiment described above, the coil spring 56 was provided as the urging member, but any type of spring may equally be used, such as a compression spring or a tension spring. Furthermore, the use of springs in forms other than the form of the coil spring 56 (e.g. leaf springs etc.) is also permitted as other urging members.

In the second mode of embodiment described above, the linking member 72 was provided as a single piece on the upper surface of the housing support part 22 of the main body 21, but it may equally be provided at another position on the main body 21. Furthermore, the linking member 72 does not necessarily need to be provided as a single piece with the main body 21, and it may be provided as a piece produced separately. Furthermore, the shape of the linking member 72 is not limited to what was described in relation to the second mode of embodiment above, and it may be modified in any way.

In the third mode of embodiment described above, the feed-out belt 82 was used as the feed-out member. A different type of rolling member to the feed-out belt 82 (e.g. a feed-out roller, etc.) may be used instead, and this rolling member may be made to roll while the guidewire 1 is pinched between said rolling member and the eliding contact surface 59.

In the first to third modes of embodiment described above, the rubber ring 35 was used as the guidewire fixing member, but this does not necessarily imply a limitation. For example, a ring-shaped member made of a material other than rubber, or a rubber member having a shape other than a ring shape may also be used. That is to say, the material and shape of this member are unimportant, provided that it is a member which can secure or release the guidewire 1 by contact with or separation from the guidewire.

In the first to third modes of embodiment described above, two water-retention members were provided, namely the water-retention member 52 on the feed-out member side and the water-retention member 57 on the sliding contact part 58 side, but the water-retention member 57 on the sliding contact part 58 side may be omitted.

In the first to third modes of embodiment described above, the arm part 31 extending in an arcuate shape and the holding part 32 were provided, but they may be omitted.

Moreover, the following technical concepts which can be understood from the modes of embodiment of the present invention may be mentioned.

(1) The fact that in the abovementioned means 3, the feed-out block also functions as a guidewire fixing member for fixing the guidewire.

(2) The fact that in any one of the abovementioned means 1 to 6, the arm part extending downwards in an arcuate shape is provided projecting from the lower surface of the main body, and the holding part for holding the housing is provided at the tip end of the arm part.

(3) The fact that in any one of the abovementioned means 1 to 6, the projection is provided on the main body close to the base end opening of the guidewire support part, and the rubber ring for securing or releasing the guidewire is attached correspondingly to the position of the projection.

KEY TO SYMBOLS

1 . . . guidewire
2 . . . housing
11, 11A, 71, 81 . . . guidewire insertion aid
21 . . . main body
22 . . . housing support part
26 . . . guidewire support part
28 . . . sliding contact part
29 . . . sliding contact surface 42 ... feed-out member support part
43 ... guide part
51 ... feed-out block serving as feed-out member
52, 57 ... water-retention member
56 ... coil spring serving as urging means
72 ... linking member
82 ... feed-out belt serving as feed-out member

The invention claimed is:

1. A guidewire insertion aid, comprising:
a guidewire;
a housing supporting the guidewire;
an insertion device secured to the housing and including:
   a body having a sliding contact surface disposed between a proximal end of the body and a distal end of the body; and
   a feed-out member movably supported on the body, the feed-out member having a water retention member disposed facing the sliding contact surface of the body and being selectively movable to advance the guidewire between the water retention member of the feed-out member and the sliding contact surface of the body, the water retention member being water retentive to lubricate the guidewire as a result of contact between the water retention member and the guidewire,
   wherein the body defines a guide that extends longitudinally along the body above the sliding contact surface, the feed-out member being movably secured to the guide to permit the selective longitudinal advancement of the guidewire upon the longitudinal advancement of the feed-out member longitudinally along the guide; and
an urging member secured to the feed-out member to urge the feed-out member towards the proximal end of the body.

2. The guidewire insertion aid of claim 1, wherein the housing is detachably secured to the proximal end of the body.

3. The guidewire insertion aid of claim 1, further comprising a guidewire support secured to the distal end of the body, wherein the guidewire support is substantially cylindrically shaped.

4. The guidewire insertion aid of claim 3, wherein the diameter of the guidewire support decreases at a distal end of the guidewire support.

5. The guidewire insertion aid of claim 1, wherein the feed-out member and the body each include a latching protrusion extending therefrom, the urging member being securable to each latching protrusion to provide a spring force to the feed-out member to urge the feed-out member toward the proximal end of the body.

6. The guidewire insertion aid of claim 5, wherein the guide includes a curved part at a distal end of the guide, the curved part maintaining the feed-out member in a distal position when the latching protrusion secured to the feed-out member is positioned in the curved part.

7. The guidewire insertion aid of claim 6, wherein the curved part extends downwardly such that when the latching protrusion secured to the feed-out is positioned in the curved part, the feed-out member engages the guidewire to maintain the guidewire in a fixed position.

8. The guidewire insertion aid of claim 1, further comprising a flexible linking member secured between the feed-out member and the body.

9. The guidewire insertion aid of claim 8, wherein the linking member includes a curved portion that deforms as the linking member moves between extended and contracted positions.

10. The guidewire insertion aid of claim 1, wherein the feed-out member is an endless feed-out belt having the water retention member on an outer peripheral surface of the feed-out belt, the feed-out belt being supported on the body so that the feed-out belt moves circumferentially.

11. The guidewire insertion aid of claim 10, wherein the feed-out belt is secured to a pair of supports having winding protrusions extending therefrom, the feed-out belt moving around the winding protrusions to move the feed-out belt circumferentially.

12. The guidewire insertion aid of claim 1, wherein the sliding contact surface includes a second water retention member.

13. The guidewire insertion aid of claim 1, wherein the body includes a rib extending longitudinally along a bottom surface of the body to increase the rigidity of the body.

14. The guidewire insertion aid of claim 1, wherein the body includes a projection at the distal end of the body adjacent a guidewire support, the projection having a ring secured to the projection, the ring being positionable between first and second orientations, in the first orientation, the ring inhibits advancement of the guidewire through the guidewire support, in the second orientation, the ring permits advancement of the guidewire through the guidewire support.

15. The guidewire insertion aid of claim 1, wherein the feed-out member includes a plurality of anti-slip protrusions.

* * * * *